(12) United States Patent
Janssens

(10) Patent No.: US 11,401,811 B2
(45) Date of Patent: Aug. 2, 2022

(54) GAS OR FLUID DRIVEN MECHANICAL STEPPER MOTOR

(71) Applicant: Eindhoven Medical Robotics B.V., Eindhoven (NL)

(72) Inventor: Marc Janssens, Eindhoven (NL)

(73) Assignee: Eindhoven Medical Robotics B.V., Eindhoven (NL)

( * ) Notice: Subject to any disclaimer, the term of this patent is extended or adjusted under 35 U.S.C. 154(b) by 0 days.

(21) Appl. No.: 17/254,183

(22) PCT Filed: Jun. 19, 2019

(86) PCT No.: PCT/NL2019/050381
§ 371 (c)(1),
(2) Date: Dec. 18, 2020

(87) PCT Pub. No.: WO2019/245370
PCT Pub. Date: Dec. 26, 2019

(65) Prior Publication Data
US 2021/0270135 A1     Sep. 2, 2021

Related U.S. Application Data

(60) Provisional application No. 62/687,532, filed on Jun. 20, 2018.

(51) Int. Cl.
*F01B 3/04* (2006.01)
*F15B 11/12* (2006.01)

(52) U.S. Cl.
CPC ............ *F01B 3/045* (2013.01); *F15B 11/127* (2013.01)

(58) Field of Classification Search
CPC .......... F15B 11/127; F01B 3/045; F01B 3/04; F16H 25/125
See application file for complete search history.

(56) References Cited

U.S. PATENT DOCUMENTS

| 3,824,420 A | 7/1974 | Stegeman et al. |
| 4,129,064 A | 12/1978 | Fahim et al. |

(Continued)

FOREIGN PATENT DOCUMENTS

| FR | 2290779 A1 | 6/1976 |
| JP | 2009108993 A | 5/2009 |

(Continued)

OTHER PUBLICATIONS

International Search Report dated Sep. 30, 2019 for PCT/NL2019/050381.

(Continued)

*Primary Examiner* — F Daniel Lopez
(74) *Attorney, Agent, or Firm* — Suiter Swantz pc llo

(57) ABSTRACT

Stepper motor with a housing 1,2,4,6,16, in which a cylindrical rotor 11,15 fixed on a central shaft 12 can rotate but not translate along an axial direction. There are cylindrical translators 9, 14 on both sides of the rotors 11, 15, where the translators 9, 14 are sealed fit in a cylindrical space within the housing 6 and around the central shaft 12 and where the translators 9, 14 can only translate in an axial direction, where in one axial position of a translator 9, 14 a set of triangular asymmetric teeth 20 located on the translator 9, 14 can interact and fit into a set of triangular asymmetric teeth 21 on the rotor 11, 15, where the shape of the teeth 21 on both sides of the rotor 11, 15 is symmetric and where one of the sets of teeth 20, 21 between one translator 9 (14) and the rotor 11 (15) and a set of teeth 20, 21 between the other translator 9 (14) and the rotor 11 (15) are tangentially shifted, i.e. offset over a length equal to half the width of a tooth 20, 21 and where the translators 9, 14 can be moved by a pressure difference between the part of the cylindrical space between the housing 6 and a translator 9, 14 and the (Continued)

Figure 1:
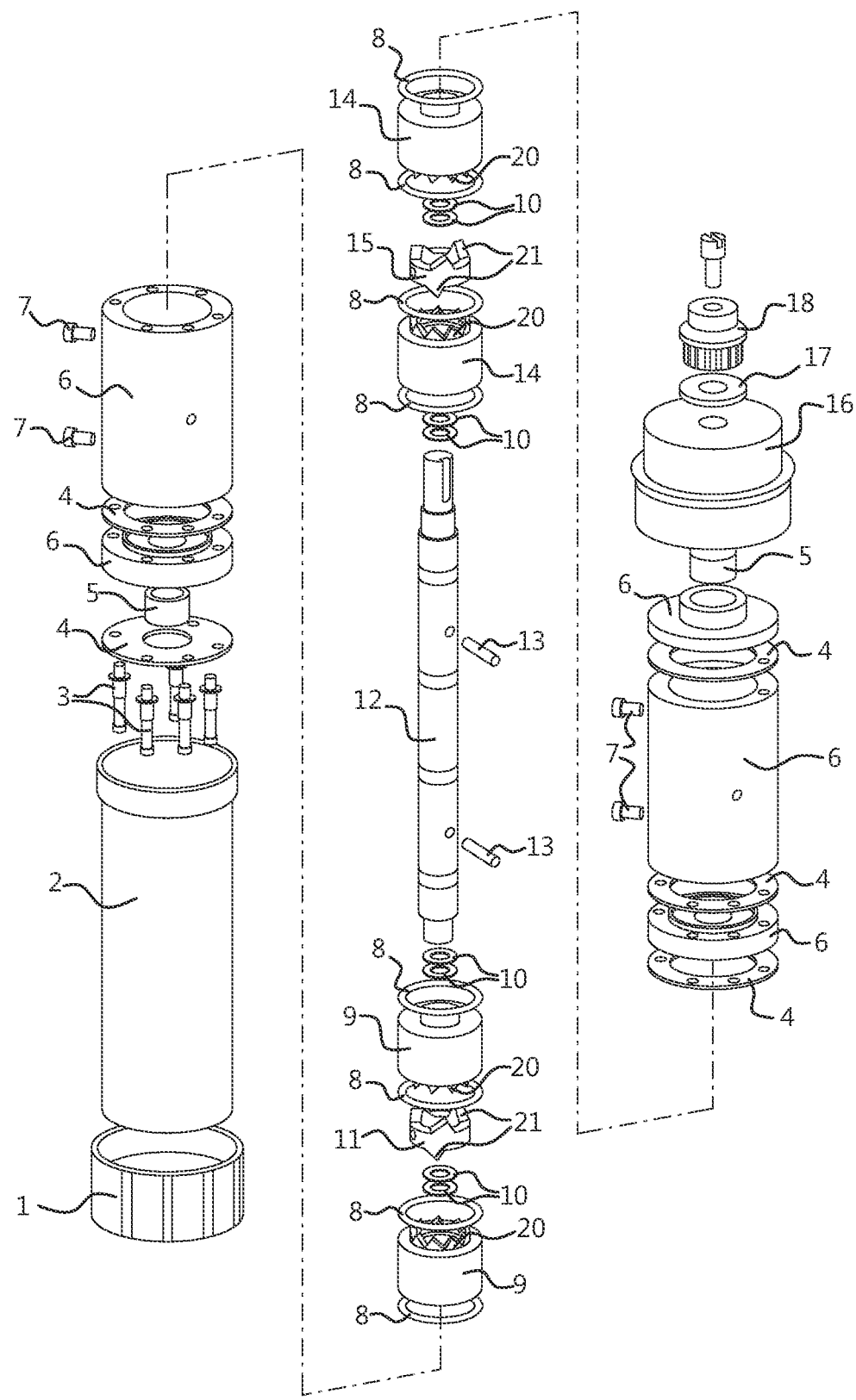

part of the cylindrical space between the translator 9, 14 and the rotor 11, 15.

9 Claims, 5 Drawing Sheets

(56) References Cited

U.S. PATENT DOCUMENTS

| | | | |
|---|---|---|---|
| 4,175,589 | A | 11/1979 | Nakamura et al. |
| 5,787,981 | A | 8/1998 | Taylor |
| 7,299,740 | B2 * | 11/2007 | Adams .................... F04B 9/047 92/71 |
| 9,522,083 | B2 | 12/2016 | Underwood et al. |
| 2005/0124452 | A1 | 6/2005 | Stoianovici et al. |
| 2005/0155443 | A1 | 7/2005 | Krozek |
| 2006/0053830 | A1 | 3/2006 | Adams |
| 2006/0090638 | A1 | 5/2006 | Santiyanont |
| 2008/0298989 | A1 | 12/2008 | Keays |

FOREIGN PATENT DOCUMENTS

| | | | |
|---|---|---|---|
| JP | 2011241970 | A | 12/2011 |
| WO | 2014195656 | A1 | 12/2014 |
| WO | 2018038608 | A1 | 3/2018 |

OTHER PUBLICATIONS

WikipediA, "Stepper Motor", https://en.wikipedia.org/wiki/Stepper_motor, last edited Nov. 29, 2020.

\* cited by examiner

Fig. 3A
Fig. 3B
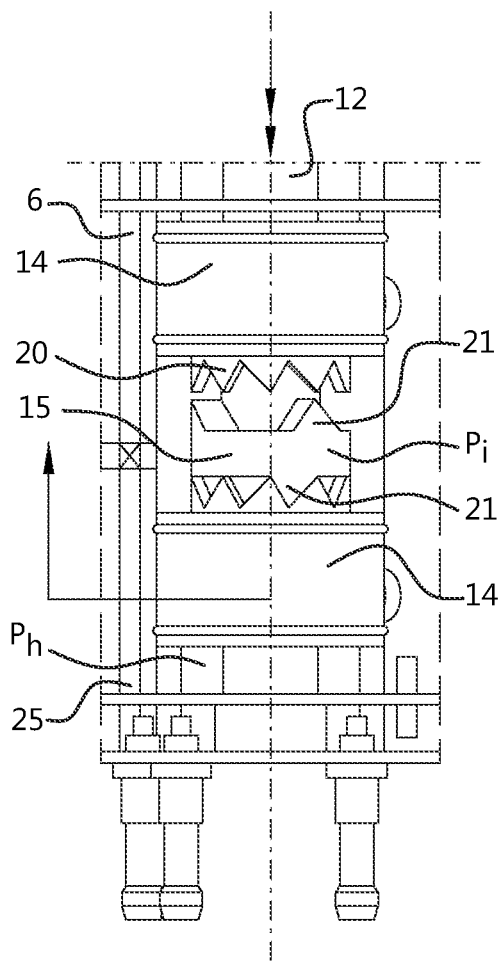
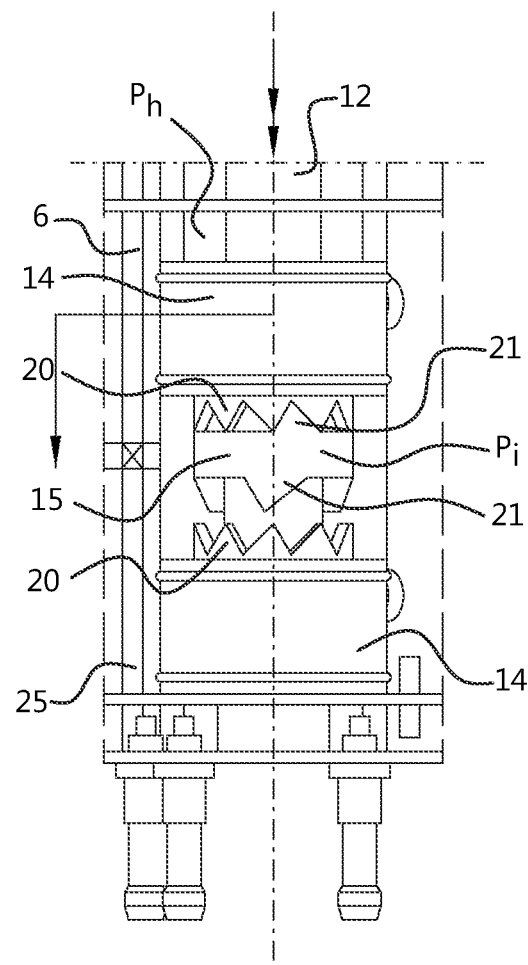

GAS OR FLUID DRIVEN MECHANICAL STEPPER MOTOR

The invention relates to a stepper motor with a housing, in which a cylindrical rotor fixed on a central shaft can rotate but not translate along an axial direction. The rotor on a stepper motor is fixed in an axial direction. Such stepper motors are well known and widely used (see https://en.wikipedia.org/wiki/Stepper_motor). Known stepper motors are driven by electromagnetic forces, for instance by having a magnetic rotor and by supplying an electric current through coils in the housing. There are however environments where it is not possible to use electromagnetic forces. This can be the case for instance in medical operating rooms where a stepper motor in a surgical instrument is used during surgical operations while using a continuous MRI (Magnetic Resonance Imaging) scanning to locate a tool on the surgical instrument. A surgical instrument working under such conditions cannot have electromagnetic stepper motors, since the strong magnetic fields used during the MRI scan would interfere with the stepper motor and cause it to malfunction. Also the MRI scan would be compromised by the presence of an electromagnetic motor. Also in for instance chemical plants where highly flammable gases or liquids are used it is not recommended to use stepper motors that depend on electricity, since this might cause sparks that can lead to dangerous situations.

According to the invention there are cylindrical translators on both sides of the rotor, where the translators are sealed fit in a cylindrical space within the housing and around the central shaft and where the translators can only translate in an axial direction, where in one axial position of a translator a set of triangular asymmetric teeth (wherein each tooth of the set of triangular asymmetric teeth is triangular asymmetric) located on the translator can interact and fit into a set of triangular asymmetric teeth on the rotor (wherein each tooth of the set of triangular asymmetric teeth on the rotor is triangular asymmetric), where a set of teeth at one side of the rotor is symmetric to a set of teeth on another side of the rotor and either the set of teeth of one of the translators and the set of teeth of the other of the translators are tangentially shifted over a length equal to half the width of a tooth, or one of the sets of teeth of the rotor and another of the sets of teeth of the rotor are tangentially shifted over a length equal to half the width of a tooth and where the translators can be moved by a pressure difference between the part of the cylindrical space between the housing of the one or the other of the translators and the part of the cylindrical space between that translator and the rotor. The two translators are moved by a pressurized gas, preferably air or a fluid in such a way that their teeth in turn engage and disengage with the teeth on different sides of the rotor. When one translator engages, the other will be disengaged. The triangular asymmetric teeth are asymmetric, i.e. one flank of a tooth is angled differently, i.e. has a shorter length as measured along the base of a tooth than the other flank. To make steps, teeth on a first translator engage with teeth on the rotor along their less steep, i.e. longer flanks. Via these flanks the translator then exerts a normal axial force and a rotational tangential force on the rotor so that the rotor rotates until the teeth on both surfaces fit into each-other, i.e. interlock. Thus the rotor is rotated by the interacting teeth. In this way a step is made by the motor. To make a further step the first interacting translator is disengaged, i.e. moved away from the rotor and the second translator engages the rotor in a similar way. Since the sets of teeth between the second translator and the rotor are shifted over a length equal to half the width of a tooth as measured along the base of the tooth, the second translator will again engage on the corresponding long flanks of the teeth and let the rotor rotate again. Length of a flank is defined as the length along a base of a tooth and the width of a tooth is defined as the total length along the base of a tooth, i.e. the length of the short and long flank together. The sets of triangular asymmetric teeth on both sides of the rotor are symmetric (mirror symmetry). However, the teeth on both sides can be shifted tangentially. The symmetry of the sets of teeth on both sides of the rotor causes the rotor to rotate in the same direction as in the first step. Thus the motor makes another step forward. Then the process is repeated by disengaging the second translator and engaging the first translator again to make again a further step. Since the teeth between the two translators and the rotor are tangentially shifted (offset) over a length equal to half the width of a tooth, i.e. larger than the length of a shorter flank of the asymmetric teeth, the rotor rotates with every step over half the length of a tooth. Since the teeth are asymmetric and the interaction takes place on the long flank of the teeth, the rotor rotates enough, i.e. more than the length of the shorter flank, so that the two translators in turn interact via the longer flank of the teeth on both surfaces.

The motor according to the invention is driven by pressurized gas or liquid. The translators are sealed fit in a cylindrical space within the housing and around the central shaft, i.e. like pistons in a bore. This means a pressure can be applied to one base surface of the cylindrical translator independent from the pressure on the other base surface of the translator. By applying a pressure difference across the base surfaces of a translator, i.e. by applying a higher pressure to a base surface on one side of a translator than to a base surface on the other side of the same translator, the translator moves in the direction of the lower pressure. By controlling these pressures a translator moves either towards or moves away from the rotor. The rotor itself is axially fixed in one position and is not affected in an axial direction by the pressures. By alternating these pressures the translators can in turn engage or disengage the rotor and so let the rotor make steps. The controlling of the pressures can be done by conventional flow control modules. These are often using electricity to control pressures, but the control devices can be placed outside the apparatus used, for instance outside an MRI scanner, or outside a danger zone in a chemical plant.

The stepper motor can have the same number of teeth on all sets of teeth. Preferably the stepper motor has one set of teeth on a translator or rotor, that has only three teeth evenly divided around the circumference. The flanks of the interacting teeth slide along each-other and create frictional losses. By having only three teeth evenly divided along the circumference these frictional losses are minimized, while the three teeth evenly divided along the circumference avoids any unbalance in the transfer of power to the rotor.

The shift (offset) of one set of teeth can be done in a translator or on the rotor. Preferably the stepper motor according to the invention has teeth on one side of the rotor that are tangentially shifted with respect to the teeth on the other side of the rotor. This way of manufacturing is easier since the shift is realized on one workpiece with greater accuracy and is not dependent on tolerances for instance in the guidance of the translators.

The stepper motor turns into one direction. The direction depends on the geometry of the asymmetric teeth. By taking an antisymmetric geometry, i.e. reversing all long and short flanks into short and long flanks the motor will step in the other direction. Preferably the stepper motor comprises two combinations of a rotor with two translators, where the combinations are anti-symmetric to each-other. In that way the stepper motor can turn in two directions, i.e. clock wise and anti-clock wise. One of the translators—rotor combinations is then used for stepping, while in the other combination the translators are disengaged from the rotor, so that the shaft is free to move with the activated combination.

The stepper motor can be driven by a gas or fluid by pressurizing and depressurizing the part of the cylindrical space between the housing and a translator and the part of the cylindrical space between a translator and the rotor. As a fluid, water or a special hydraulic oil can be used. Using fluids is more complicated, since fluids are not compressible and thus the fluid needs to be removed or supplied when a space between housing, translator and the rotor is made smaller or larger. This is complex and rather slow. Preferably the stepper motor is driven by a gas. Many gases are available that can be used to drive the stepper motor, such as nitrogen, air or an inert gas such as helium.

When a gas is used it is advantageous when the space between the rotor and one translator is connected to the space between the rotor and the other translator. This means that the space between the translators can be filled with an intermediately pressurized gas. This gas than functions as a gas spring between the translators. When high pressure is applied to the space between the housing and the back surface of one translator, that translator then moves towards and interacts with the rotor, overcoming the intermediate pressure between the translator and the rotor. The back surface of the second translator is then held at a pressure lower than the intermediate pressure in between the two translators. The second translator is then moved away from the rotor and pressed against the housing. By reversing the pressures in the spaces between the housing and the back surfaces of the two translators, the first translator moves away from the rotor and the second translator moves towards and interacts with the rotor. In that way the motor can make steps. Convenient pressures are: for the intermediate pressure between the two translators 200 kPa (2 bar); for the high pressure 500 kPa (5 bar) and for the pressure lower than 200 kPa, 100 kPa (1 bar), i.e. atmospheric pressure.

The stepper motor can in principle be made from any material that is strong enough to withstand the forces occurring. For use in an MRI scanner the stepper motor is preferably made from a non-ferromagnetic material, such as a plastic or aluminium. If MRI transparency is also important the motor can be made from Polyether ether ketone (PEEK).

The invention further relates to an MRI scanner in which a stepper motor is used according to one of the preceding claims, where the motor is made from a non-ferromagnetic material, preferably polyether ether ketone (PEEK).

The invention also relates a method to rotate an axis of a stepper motor as described above in surgical instruments or chemical plants by alternately applying a high pressure gas to the space between the housing and the back surface of one of the translators and a low pressure gas to the space between the housing and the back surface of the other translator, while keeping the space between the translators and the rotor at an intermediate pressure. This way the one translator moves towards and engages with the rotor, while the other translator moves away and is disengaged from the rotor. The high and low pressures are then reversed so that the other translator moves towards the rotor and the one translator moves away from the rotor. The space(s) between the translators and the rotor are held permanently at an intermediate pressure.

DESCRIPTION FIGURES

Figure 2:
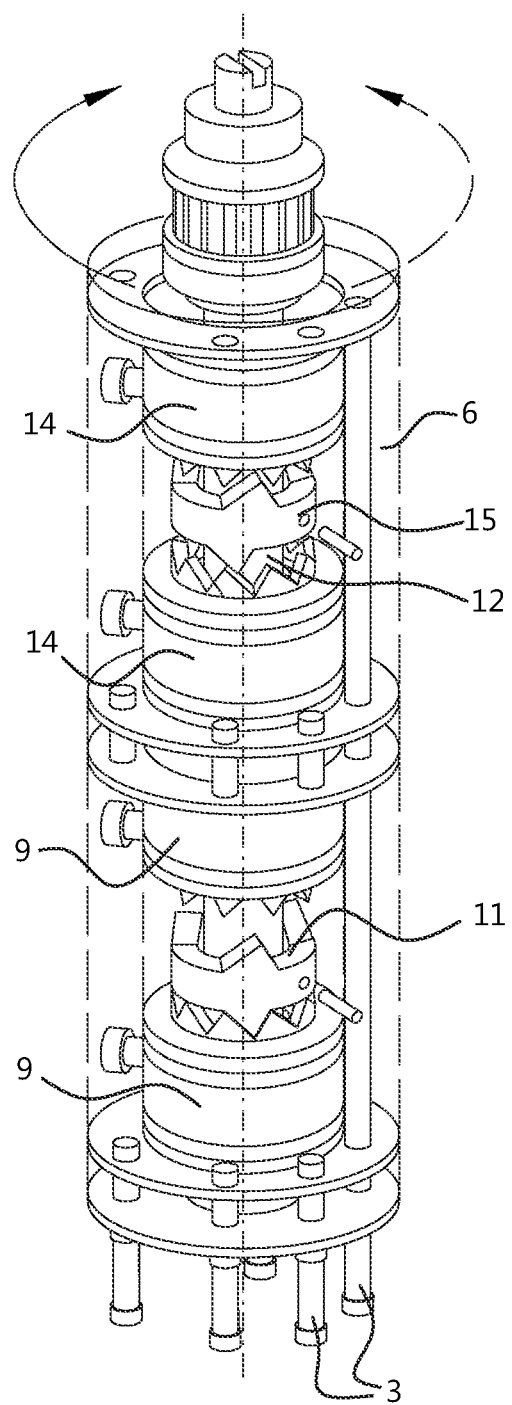
Figure 4:
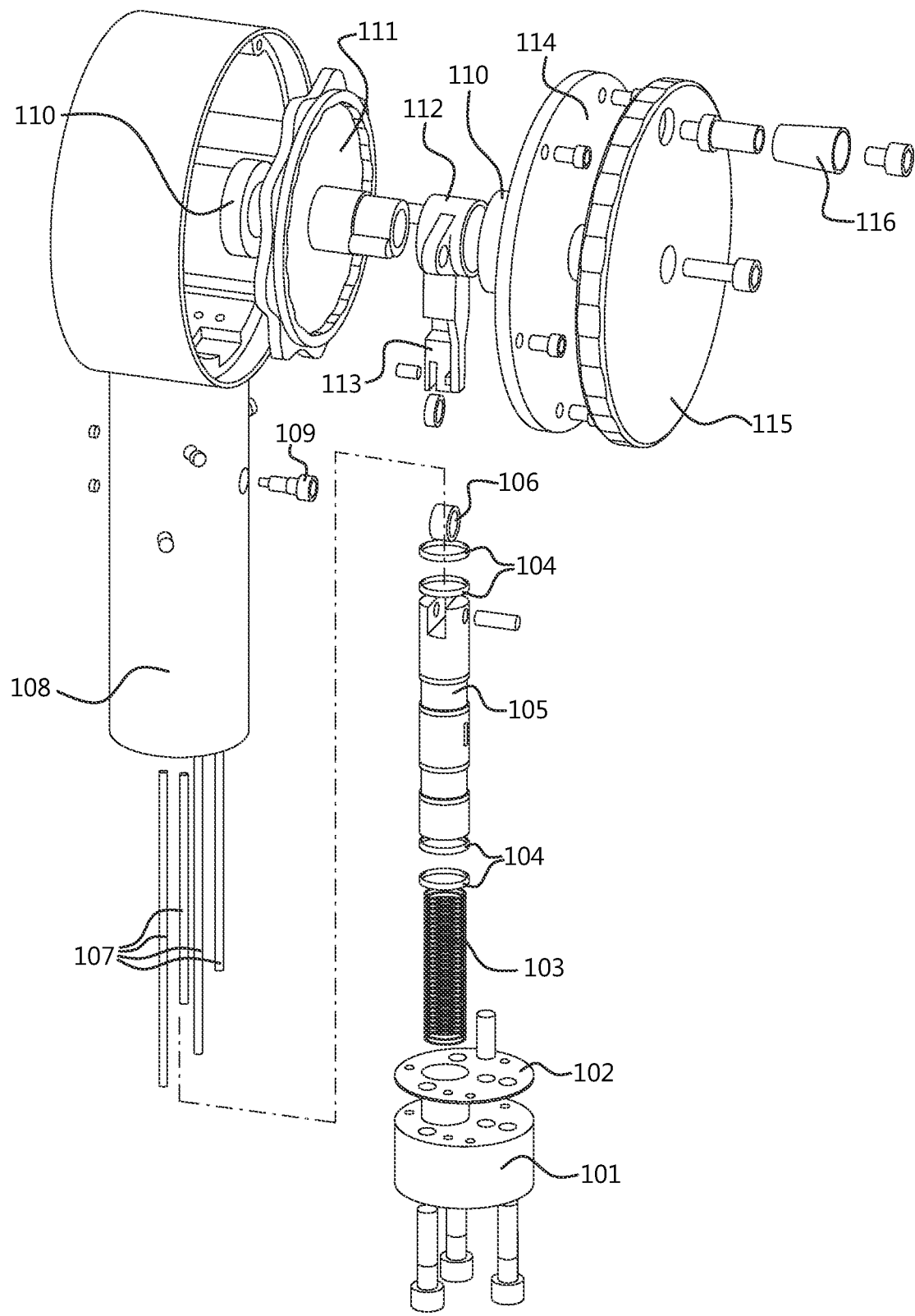
Figure 5:
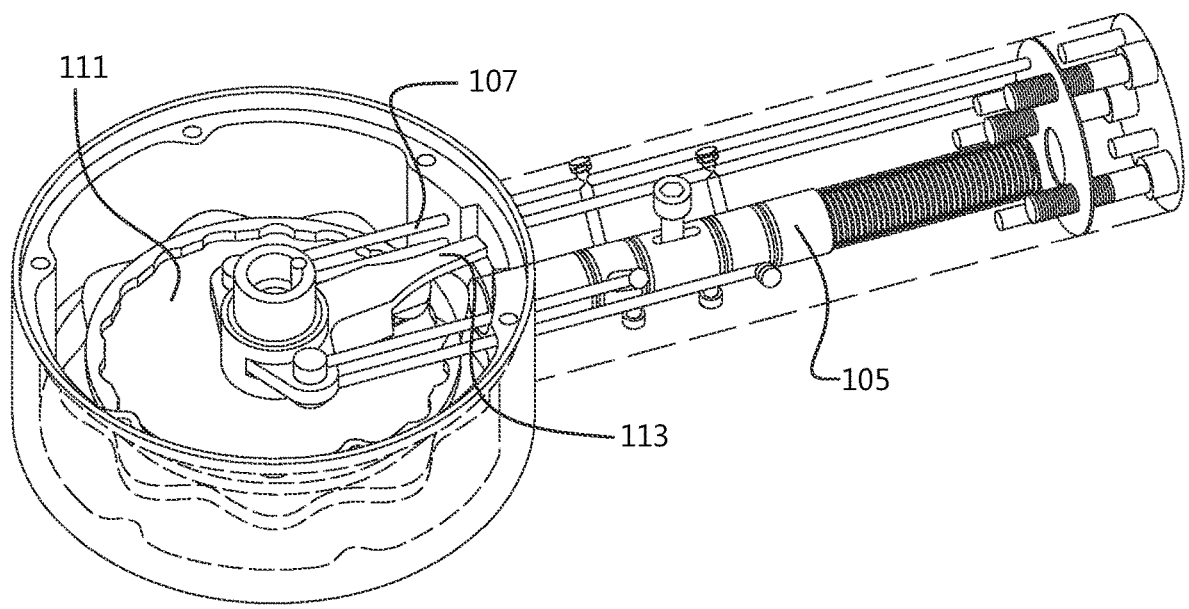
Figure 6:
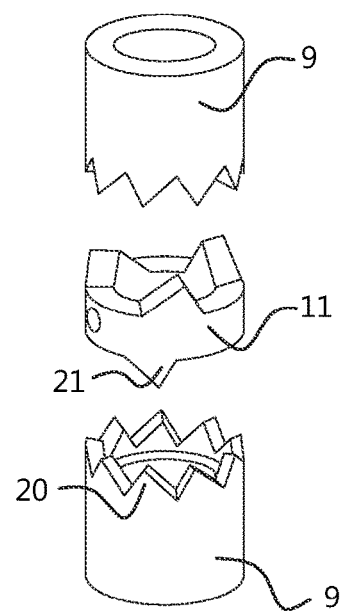

The invention is further explained with the help of the following drawing in which FIG. 1 shows an exploded view of the complete stepper motor assembly, FIG. 2 shows the stepper motor as assembled with a translucent housing and its enclosure removed, FIG. 3 shows the operation of the stepper motor with in FIGS. 3a and 3b different positions of the two translators, FIG. 4 shows an exploded view of a flow control module for applying pressures to the stepper motor, FIG. 5 shows the flow control module, and FIG. 6 shows an exploded portion of the motor assembly as shown in FIG. 1.

FIG. 1 shows an exploded view of the complete motor assembly, with: 1. enclosure closing ring; 2. enclosure bottom; 3. connection hose pillars; 4. housing gasket; 5. shaft bearing; 6. housing segment; 7. rotation lock key for translator; 8. translator—housing seal ring; 9. translator (clockwise); 10. translator—shaft seal ring; 11. rotor (clockwise); 12. shaft; 13. rotor lock pin (to shaft); 14. translator (counter clockwise); 15. rotor (counter clockwise); 16. enclosure top; 17. pulley flange; 18. pulley.

The stepper motor has a housing 1,2,4,6,16, in which a cylindrical rotor 11, 15 is fixed with rotor locking pins 13 on a central shaft 12. The rotors 11, 15 can rotate but not translate along an axial direction via bearings 5. The stepper motor comprises cylindrical translators 9, 14 on both sides of the rotor 11, resp. 15, where the translators 9, 14 are sealed fit in a space inside cylinder 6, which is part of the housing and around the central shaft 12 and where the translators 9, 14 can only translate in an axial direction because of the keys 7, where in one axial position of a translator 9, 14 a set of triangular asymmetric teeth 20 located on a translator 9, 14 can interact and fit into a set of triangular asymmetric teeth 21 on the rotor 11, 15. Here the fit means that the teeth 20 and 21 are anti symmetric, i.e. where one tooth 20, 21 has a tip, the other tooth 21, 20 has a valley. The shape of the teeth on both sides of the rotor 11, 15 is symmetric (mirror symmetry). One of the sets of teeth 20, 21 between one of the translators 9 (14) and the rotor 11 (15) and a set of teeth 20, 21 between the other translator 9 (14) and the rotor 11 (15) are tangentially shifted (offset) over a length equal to half the width of a tooth 20, 21. Where length is defined as the length along the base of the teeth. In the example the sets of teeth 21 on the different sides of the rotors 11, 15 are shifted. Instead of shifting the teeth on the two sides of the rotor with respect to each-other, it is also possible to not shift the teeth on the two sides of the rotor, but shift the sets of teeth on the two translators corresponding to a rotor with respect to each-other.

The translators 9, 14 can be moved by a compressed gas or fluid by pressurizing and depressurizing the part of the space inside cylinder 6 between the housing and a translator 9, 14 and the part of the space inside the cylinder 6 between a translator 9, 14 and the rotor 11, 15. In this embodiment the set of teeth 21 on the rotors 11, 15 have only three teeth 21 evenly divided around the circumference, where the teeth 21 on one side of the rotor 11, 15 are tangentially shifted with respect to the teeth 21 on the other side of the rotor 11, 15. The translators 9, 14 comprise nine teeth. In this embodiment the stepper motor comprises two combinations of a rotor 11, 15 with two translators 9, 14, where the combinations 9, 11 and 14, 15 are anti-symmetric to each-other. This means that the long and short flanks of the teeth 20, 21 are reversed, so a long flank in the combination 9, 11 becomes a short flank in combination 14, 15 and vice versa. The gas or fluid is provided via hose pillars 3.

The stepper motor shown in FIG. 1 is designed to operate with a gas, in this case compressed air. The motor has an axial length of 93.3 mm (excluding hose connectors 3) and an outer diameter of 27 mm. The internal working parts are sealed by an enclosure 1, 2, 16 (see FIG. 1) to minimize contamination. This motor is designed to be slender, though still able to provide enough torque to operate for instance an electrode drive, i.e. a drive for inserting an electrode for deep brain stimulation. If more torque is required this can easily be done by increasing the size of the motor. Use of excessively high air pressure is undesirable, so operating pressures are set to not exceed 500 kPa (5 bars). The motor can be used with a gear drive, for instance the pulley 18 on the motor can drive a second pulley via a timing belt.

FIG. 2 shows the motor without its enclosure 1, 2, 16 and with its housing segments 6 translucent. The top half of the motor, with a set of translators 14 and a rotor 15 fixed to the shaft, takes care of the counter clockwise rotation of the shaft 12. The bottom half with two translators 9 and a rotor 11 fixed to the shaft 12, is for clockwise rotation.

FIGS. 1 and 2 show that the translators 9, 14 can only translate in the motor housing 6; their rotation is fixed with keys 7 in the housing 6. The translation of translators 9, 14 is driven pneumatically, using a switchable high pressure supply of 500 kPa (5 bar) for motion towards the corresponding rotor 11, 15 and a continuous intermediate pressure supply of 200 kPa (2 bar) to the space within cylinder 6 between the rotor 11, 15 and the translators 9, 14. The latter space around the rotors 11, 15 acts as an air spring that pushes the translators 9, 14 away from the rotors 11, 15 when the high pressure is switched off. The translators 9, 14 are sealed fit inside the housing 6 using PTFE (polytetrafluoroethene) sealing rings 8 along both the outer and inner circumference of all translators 9, 14. These rings 8 are intended to prevent blow-by leakage, whilst minimizing the friction of the translators 9, 14 along the wall of housing 6 and shaft 12. The rotors 11, 15 are fixed on the shaft 12 with pins 13. The translators 9, 14 have nine asymmetric teeth 20 and the rotors 11, 15 have a set of three asymmetric teeth 21 on both of their base surfaces. The sets of teeth 21 on the rotor 11, 15 are offset, i.e. tangentially shifted over a length equal to half the width of a tooth. In this case the offset is half a tooth, i.e. 20 degrees.

The motor has five pneumatic hose connectors 3. One connector 3 is for the continuous low pressure air 200 kPa supply to the air spring orifices, i.e. the space between the translators 9, 14 and the rotors 11, 15. The rotor 11, 15 does not have a seal along its circumference, hence the spaces between the rotors 11, 15 and the corresponding translators 9, 14 are connected. The other four connectors 3 feed on/off high pressure air (500 kPa) to their respective translators. As both combinations of translator rotor operate in a similar way, only the top one with translators 14 and rotor 15 will be discussed in more detail.

FIG. 3a shows that when a high pressure $P_h$ is applied to the space between the housing 6 and the bottom translator 14 then the bottom translator 14 moves towards the rotor 15, the flanks of three of its teeth 20 will engage with those of the three teeth 21 of the rotor 15. As the bottom translator 14 moves on, the engaged longer flanks of the translator 14 and rotor 15 will slide relatively, resulting in a rotation of the rotor 15 and shaft 12. FIG. 3b shows that by switching off the high pressure $P_h$ the bottom translator 14 will be pushed back, away from the rotor 15 by the intermediate pressure $P_l$ between the rotor 15 and the translator 14. A high pressure $P_h$ is simultaneously applied to the other (top) translator 14. That one moves towards the rotor 15 and the teeth 20, 21 engage and rotate the rotor 15 further. The rotor 15 will perform a stepping rotation with 20 degree increments. The cycle is then repeated. The switching on/off of the high pressure $P_h$ is realized with a dedicated flow control module. The indexing accuracy of the operating mechanism is not affected by wear. In this example the high pressure $P_h$ is 500 kPa, the intermediate pressure $P_l$ is 200 kPa and when the high pressure $P_h$ is switched off the pressure is 100 kPa, i.e atmospheric pressure. Thus the air pressure $P_l$ between the rotor and the translators is intermediate between the lower atmospheric pressure and the high pressure $P_h$.

FIG. 3 shows how for each translator 9, 14, the air is led from a dedicated connector 3 at one end of the motor, through channels 25 in the housing, to the corresponding translator 9, 14. Whilst one translator rotor combination 9, 11 (14, 15) is in operation, the other pair 14, 15 (9, 11) should remain retracted from its rotor. This is realized by the continuous intermediate pressure between the rotors 11, 15 and the translators 9, 14 and by not applying any high pressure to the retracted translators.

An alternative way of driving the stepper motor is to use a soft vacuum and high pressure. The space between the rotor and translators is then at atmospheric pressure and the translators are moved in a similar way as discussed before by alternatively applying high pressure air and the soft vacuum.

The high and low pressure gases or fluids can be supplied by conventional flow control modules outside the critical environment.

The motor as described in the embodiment can be produced out of both plastics and metals, allowing for its use in an MRI environment or when electromagnetic interference is an issue. In this example the motor was produced from a plastic, a Polyether Ether Ketone (PEEK). This material has excellent mechanical qualities, that make it very suitable for use in a stepper motor in an MRI environment.

A manual flow control module for allowing the motor to make steps is now described with reference to FIGS. 4 and 5. FIG. 4 shows an exploded view of a flow control module in which: 101. handgrip end; 102. gasket; 103. piston preload spring; 104. piston seal ring (PTFE); 105. piston; 106. cam follower bearing; 107. air channel needle; 108. handgrip/housing; 109. piston rotation lock pin; 110. wave disc bearing; 111. wave disc; 112. air output selection lever; 113. indexing spring plunger; 114. wave disc bearing cover; 115. handle wheel; 116. handle.

The air supplies required for the stepper motor according to FIG. 1, are a continuous feed of low pressure air (200 kPa), and a feed of high pressure air (500 kPa) alternating over two times two lines corresponding to two lines for the set of translators 9 and two lines for the set translators 14 driving the motor rotation. The low pressure air supply is connected directly to the motor; the alternating high pressure air supply is realized with a manual flow control module shown in FIGS. 4 and 5. A change in rotation direction of the stepper motor, i.e. a change in using a set of translators from 9 to 14 or vice versa is achieved by switching the set of two lines over which the alternating feed of high pressure air is sent (each translator pair 9, 14 corresponds to one set of two lines).

Alternating the high pressure air feed is achieved with a translating piston 105. In moving through its housing's bore, it switches the high pressure air feed over the two channels of each output pair. The piston motion is driven by a wave disc 111, which in turn is rotated with the handle wheel 115. To ensure the piston 105 follows the wave profile on the wave disc 111, it is preloaded against the disc 111 with a coil spring 103. The piston 105 is located in the handgrip 108 which allows the user to conveniently hold the module with one hand, whilst rotating the handle 116 or handle wheel 115 with the other hand.

When the rotation direction of the handle wheel 115 is changed from clockwise to counterclockwise (or vice versa), the output pair over which the air is sent to the motor is switched accordingly. A lever 112, placed coaxially with the wave disc 111, operates two pairs of needles 107 which can slide in the air channels inside the handgrip 108. Starting from a neutral position, sliding a needle 107 slightly further into its channel will block the airflow running from the piston 105 towards the air output. When the needle 107 is retracted slightly from its channel, the airflow mentioned will be freed up completely. The two extreme positions of the needle are distinguished by a rotation of 18 degrees of the lever (plus and minus 9 degrees starting from a neutral position).

The rotation of the wave disc 111, and there with the handle wheel 115, is indexed with a spring plunger 113 which is integrated in the air output selection lever 112. When the lever 112 is in either of its extreme positions and the wave disc 111 is rotated further in the corresponding direction, the spring plunger 113 provides indexing of the rotation. When the wave disc 111 is now rotated in the other direction, the spring plunger 113 will lock the rotation of the lever 112 to that of the disc 111, until the lever 112 reaches its other extreme position. From there on, the spring plunger 113 will again index the rotation of the wave disc 111 and handle wheel 115.

Switching the output pair over which air is sent to the motor, changes which translator pair 9 or 14 in the motor is provided with the alternating high pressure air. This effectively changes the motor's rotation direction.

The invention claimed is:

1. A stepper motor with a housing, in which a cylindrical rotor fixed on a central shaft can rotate but not translate along an axial direction, characterized in that there are cylindrical translators on both sides of the rotor, where the translators are sealed fit in a cylindrical space within the housing and around the central shaft and where the translators can only translate in an axial direction, where in one axial position of each of the translators, a respective set of triangular asymmetric teeth located on the respective translator can interact and fit into a respective set of triangular asymmetric teeth on the rotor, and where either the set of teeth of one of the translators relative to the set of teeth of another of the translators are tangentially shifted over a length equal to half the width of a tooth and the respective set of teeth at one side of the rotor is symmetric to the respective set of teeth on another side of the rotor, or one of the sets of teeth of the rotor relative to another of the sets of teeth of the rotor are tangentially shifted over a length equal to half the width of a tooth and where each of the translators is moved by a pressure difference between a part of the cylindrical space between the housing and the respective translator and a part of the cylindrical space between the respective translator and the rotor.

2. The stepper motor according to claim 1, characterized in that one set of teeth on a translator or rotor has only three teeth evenly divided around the circumference.

3. The stepper motor according to claim 1, characterized in that the teeth on one side of the rotor are tangentially shifted with respect to the teeth on the other side of the rotor.

4. The stepper motor according to claim 1, characterized in that the stepper motor comprises two combinations of a rotor with two translators, where the combinations are anti-symmetric to each-other.

5. The stepper motor according to claim 1, characterized in that the stepper motor is driven by a gas.

6. The stepper motor according to claim 5, characterized in that the space between the rotor and one translator is connected to the space between the rotor and the other translator.

7. A stepper motor for use in a MRI scanner, comprising:
the stepper motor including a housing, in which a cylindrical rotor fixed on a central shaft can rotate but not translate along an axial direction, characterized in that there are cylindrical translators on both sides of the rotor, where the translators are sealed fit in a cylindrical space within the housing and around the central shaft and where the translators can only translate in an axial direction, where in one axial position of each of the translators, a respective set of triangular asymmetric teeth located on the respective translator can interact and fit into a respective set of triangular asymmetric teeth on the rotor, and where either the set of teeth of one of the translators relative to the set of teeth of another of the translators are tangentially shifted over a length equal to half the width of a tooth and the respective set of teeth at one side of the rotor is symmetric to the respective set of teeth on another side of the rotor, or one of the sets of teeth of the rotor relative to and another of the sets of teeth of the rotor are tangentially shifted over a length equal to half the width of a tooth and where each of the translators is moved by a pressure difference between a part of the cylindrical space between the housing and the respective translator and a part of the cylindrical space between the respective translator and the rotor, where the motor is made from a non-ferromagnetic material.

8. The stepper motor according to claim 7, where the stepper motor is made from PEEK (Polyether ether ketone).

9. A method to rotate an axis of a stepper motor in surgical instruments or chemical plants, the stepper motor including a housing, in which a cylindrical rotor fixed on a central shaft can rotate but not translate along an axial direction, characterized in that there are cylindrical translators on both sides of the rotor, where the translators are sealed fit in a cylindrical space within the housing and around the central shaft and where the translators can only translate in an axial direction, where in one axial position of each of the translators, a respective set of triangular asymmetric teeth located on the respective translator can interact and fit into a respective set of triangular asymmetric teeth on the rotor, and where either the set of teeth of one of the translators relative to the set of teeth of another of the translators are tangentially shifted over a length equal to half the width of a tooth and the respective set of teeth at one side of the rotor is symmetric to the respective set of teeth on another side of the rotor, or one of the sets of teeth of the rotor relative to another of the sets of teeth of the rotor are tangentially shifted over a length equal to half the width of a tooth and where each of the translators is moved by a pressure difference between a part of the cylindrical space between the housing and the respective translator and a part of the cylindrical space between the respective translator and the rotor, comprising:

alternately applying high and low pressure gas to the first space of the one translator and low and high pressure gas to the first space of the other translator, while keeping the the second spaces permanently at an intermediate pressure.

* * * * *